United States Patent [19]

Elias et al.

[11] Patent Number: 4,890,502
[45] Date of Patent: Jan. 2, 1990

[54] SORBENT TUBE TRACE SAMPLE RELEASING APPARATUS

[75] Inventors: Lorne Elias, Nepean; André H. Lawrence, Gloucester, both of Canada

[73] Assignee: Canadian Patents and Development Limited/Societe Canadienne Des Brevets Et D'Exploitation Limitee, Ottawa, Canada

[21] Appl. No.: 376,162

[22] Filed: Jul. 7, 1989

Related U.S. Application Data

[63] Continuation of Ser. No. 268,489, Nov. 8, 1988, abandoned, which is a continuation-in-part of Ser. No. 108,532, Oct. 15, 1987, abandoned.

[30] Foreign Application Priority Data

Oct. 16, 1986 [CA] Canada ................................. 520694

[51] Int. Cl.$^4$ ............................................. G01N 35/00
[52] U.S. Cl. ................................................. 73/864.85
[58] Field of Search ........... 73/864.21, 864.81, 864.85, 73/864.87; 55/386

[56] References Cited

U.S. PATENT DOCUMENTS

| | | | |
|---|---|---|---|
| 3,205,711 | 9/1965 | Harris | 73/864.85 |
| 3,566,698 | 3/1971 | Sheppard | 73/864.85 |
| 3,735,640 | 5/1973 | Chizov et al. | 73/864.85 |
| 4,148,315 | 4/1979 | Berezkin et al. | 73/864.18 |
| 4,269,608 | 5/1981 | Sisti et al. | 73/864.85 |
| 4,294,117 | 10/1981 | Buser et al. | 73/864.85 |
| 4,414,857 | 11/1983 | Brazhnikov et al. | 73/864.87 |
| 4,612,019 | 9/1986 | Langhorst | 55/16 |

FOREIGN PATENT DOCUMENTS 1215748 4/1960 France ................................. 73/864.85

Primary Examiner—Robert R. Raevis
Attorney, Agent, or Firm—Griffin, Branigan & Butler

[57] ABSTRACT

A sorbent tube trace sample releasing apparatus comprises a tubular casing for connection at a downstream end to, say, a gas chromatograph, a spring loaded valve in the bore of the casing, a valved, purging gas inlet downstream of the spring loaded valve and a sorbent tube receiving end portion upstream thereof, surrounded by a heating coil, and fitted with an O-ring seal adjacent an upstream side of the spring loaded valve. The tubular casing is connected to a sample entry of a gas chromatograph and purging gas is fed to the gas chromatograph. The purged casing is then heated by heating coil with a sample carrying sorbent tube inserted in with the casing, spring loaded valve and sample carrying end of the sorbent tube heated, the sorbent tube is then used to open the spring loaded valve while a carrier gas is fed along the sorbent tube to release the sample. When the trace sample has been released, purging gas is fed through the purging gas inlet with the spring loaded valve closed because substantially only a portion of the casing interior needs to be purged.

2 Claims, 3 Drawing Sheets

SORBENT TUBE TRACE SAMPLE RELEASING APPARATUS

This application is a continuation of Ser. No. 268,489, filed Nov. 8, 1988 now abandoned. That application is in turn a continuation-in-part of application Ser. No. 108,532, filed Oct. 15, 1987, now abandoned. Both of these applications are incorporated herein by reference and relied upon for disclosure.

This is a continuation-in-part application of application Ser. No. 108,532, filed Oct. 15, 1987, now abandoned.

BACKGROUND

This invention relates to a sorbent tube trace sample releasing apparatus. This invention is particularly useful for the injection of a sample into gas chromatographs and other analytical instruments.

It is well known in the art that gas chromatography requires a constant flow of a stream of inert gas (called the carrier gas) be maintained through the partition column, the gas stream serving primarily to transport the chemical sample to be analyzed through the column and hence to the detector at the exit end. For the column to retain optimum efficiency and for repeatibility of results, it is important that the column be kept purged with a purging gas stream during introduction of the sample.

In conventional gas chromatographs samples are injected through a rubber septum into the gas stream with a needle syringe the samples usually being in the liquid form. However, for trace samples collected, or "preconcentrated" in adsorbent traps such as, for example, when ambient air is monitored for trace contaminants (see for example Canadian Patent No. 1,201,646, issued Mar. 11, 1986, inventors A. H. Lawrence and L. Elias), the conventional method of sample injection is not suitable because a solvent extraction step is required which is not only time consuming but results in the loss of too much sample when the sample is a trace sample.

A number of approaches have been attempted as alternatives to the conventional septum injection method, such as, for example:

Canadian Patent No. 903,519, dated June 27, 1972, T. Johns, discloses a sample injection apparatus for introducing a predetermined fluid sample into a fluid stream in a predetermined way so that such problems as baseline drift caused by slow vaporization of the sample can be avoided.

U.S. Pat. No. 3,482,450, dated Dec. 9, 1969, R. J. Harris, Sr, and R. J. Harris, Jr., discloses a sample inlet system which includes a septum and is concerned with the smooth introduction and carriage of samples into the carrier gas stream of apparatus such as gas chromatographs.

U.S. Pat. No. 3,566,698, dated Mar. 2, 1971, W. M. Sheppard, discloses a septumless inlet for chromatographs directed to overcoming the problem of the limited life of septums. Sheppard's inlet has a casing containing a spring loaded shuttle having a bore, closed at the downstream end, for receiving the open end of a syringe. The shuttle has a neck portion containing a cross bore for the escape of sample existing from the syringe in a carrier gas. When the shuttle is in a retracted position, an O-ring seal around the neck portion seals a sample outlet from the cross bore. When the shuttle is urged in a forward direction the O-ring seal seals the shuttle to the casing rearwardly of the cross-bore so that sample can be carried by the carrier gas along a sealed path to the chromatographs. While the inlet of Sheppard is useful, there are no provisions for preventing the escape of sample rearwardly around the shuttle while the shuttle is being moved forwardly from the retracted position. Consequently Sheppard's inlet is not suitable for use when the sample is a trace sample and only a very small loss of the sample as it is being transferred from the syringe to the gas chromatograph is allowable.

U.S. Pat. No. 4,294,117, dated Oct. 13, 1981, H. B. User et al., discloses a sample charger for a gas chromatograph wherein a sample in a sample holding capsule is entrained in a carrier gas and is transferred to an upstream end of an adsorption tube in an annular passage. The sample is free to flow along the annular passage in a cavity around the outside of the adsorption tube and so the charger of B user et al is not suitable for use with trace samples.

U.S. Pat. No. 4,612,019, dated Sept. 16, 1986, M. L. Langhorst, teaches that collected constituents on an adsorbent or absorbent material may be desorbed, for example, with a suitable solvent and subsequently analyzed by well-known analytical methods such as liquid or gas chromatography. Langhorst does not teach an apparatus that is suitable for releasing a trace sample from a sorbent tube for analyses in a gas chromatograph.

U.S. Pat. Nos. 3,735,640, dated May 29, 1973, Chizhov et al, and 4,414,857, dated Nov. 15, 1983, show that it is well known to use valves to control carrier gas flow to a gas chromatograph, but they do not teach an apparatus that is suitable for transferring a trace sample from a sorbent tube for analyses in a gas chromatrograph.

There is a need for a valved apparatus suitable for transferring a trace sample from a sorbent tube to a chromatograph wherein the loss of sample during the transfer is negligible.

According to the present invention there is provided a sorbent tube trace sample releasing apparatus for sample analysis, comprising;

(a) a tubular casing having an outlet at an end downstream with respect to the flow of a trace sample from the tubular casing, for connection to a sample analyzing apparatus, the tubular casing having a sorbent tube receiving portion extending downstream from an upstream, sorbent tube inlet end of the casing, a valve seating in the tubular casing and at the downstream end of the sorbent tube receiving portion, and a purging gas inlet to the casing interior and adjacent to a downstream side of the valve seating, (b) a valve seal spring loaded in an upstream direction against the valve seating, for displacement by a blunt end of the sorbent tube, (c) a closure valve connected to the purging gas inlet, (d) sealing means, adjacent an upstream side of the spring-loaded valve seal, for slidably sealing a downstream end of the sorbent tube in the sorbent tube receiving portion with the valve seal against the valve sealing, (e) heating means for heating the casing, the valve seal and the sorbent tube thereby thermally releasing a sample from a downstream end of the sorbent tube in the casing, whereby, in operation, (f) with the sorbent tube displacing the valve seal from the valve seating, the heating means heating the casing, the valve seal and the sorbent tube, thereby thermally releasing a trace sample from the sorbent tube, and carrier gas conveying released trace sample to a sample analyzing apparatus connected to the downstream end of the casing, the sealing means being adjacent an upstream side of the spring-loaded valve seal permits substantially only the heated valve seal, valve seating and casing interior downstream thereof to be contacted with released sample, so that loss of the trace sample is minimal and is encountered substantially only in a relatively small portion of the casing interior adjacent the outlet, so that (g) for purging the apparatus it is only necessary for purging gas to passed into the purging gas inlet with the valve seal closed against the valve seating, so that only the relatively small portion of casing interior is purged.

In some embodiments of the present invention the valve seating is a chamfered portion of the interior of the casing 1 and enlarged in the downstream direction, and the valve seal has a truncated-cone-shaped sealing surface which seals against the chamfer.

BRIEF DESCRIPTION OF THE DRAWINGS

In the accompanying drawings which illustrate, by way of example, an embodiment of the present invention.

Referring now to FIGS. 1 to 3, there is shown a sorbent tube trace sample releasing apparatus for sample analysis, comprising:

Figure 1:
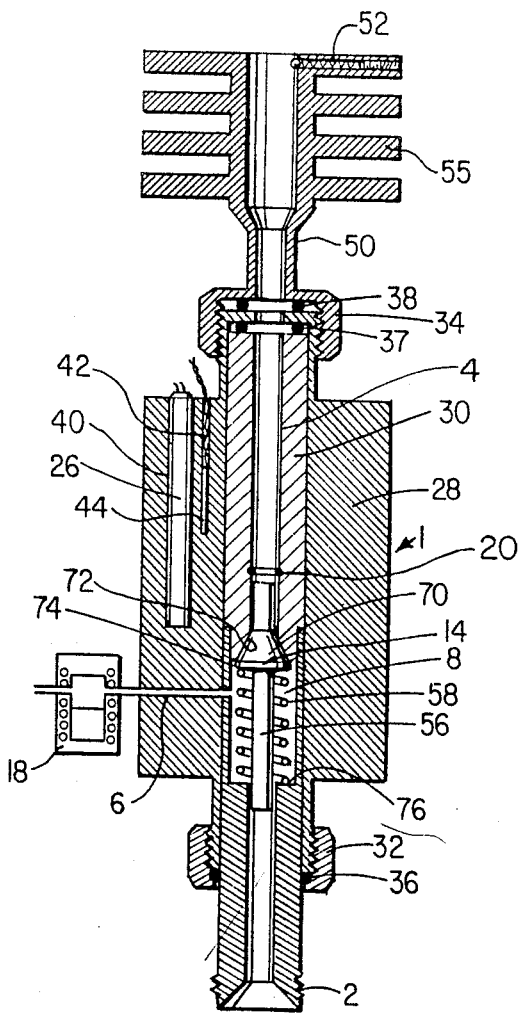
FIG. 1 is a sectional side view through the longitudinal axis of a sorbent tube trace sample releasing apparatus.

(a) a tubular casing generally designated 1 having an outlet 2 at an end downstream with respect to the flow of a trace sample (not shown) from the tubular casing 1, for connection to a sample analyzing apparatus (not shown), the tubular casing 1 having a sorbent tube receiving portion 4 extending downstream from an upstream, sorbent tube inlet end of the casing 1, a valve seating 72 in the tubular casing 1 and at the downstream end of the sorbent tube receiving portion 4, and a purging gas inlet 6 to the casing interior 8 and adjacent to a downstream side of the valve seating 72, (b) a valve seal generally designated 14 spring loaded in an upstream direction against the valve seating 72, for displacement by a blunt end of a sorbent tube 16, (c) a closure valve, in this embodiment solenoid valve 18, connected to the purging gas inlet 6, (d) sealing means, in this embodiment O-ring 20, adjacent an upstream side of the spring-loaded valve seal 14, for slidably sealing a downstream end of the sorbent tube 16 in the sorbent tube 16 receiving portion 4 with the valve seal 14 against the valve seating 72.

(e) heating means, in this embodiment cartridge heater 26, for heating the casing 1, the valve seal 14 and the sorbent tube 16 thereby thermally releasing a sample from a downstream end of the sorbent tube 16 in the casing 1, whereby, in operation, (f) with the sorbent tube 16 displacing the valve seal 14 from the valve seating, the heating means heating the casing 1, the valve seal 14 and the sorbent tube 16, thereby thermally releasing a trace sample from a sample carrying end 24 of the sorbent tube 16, and carrier gas from tube 22 conveying released trace sample to a sample analyzing apparatus (not shown) connected to the downstream end of the casing 1, the O-ring sealing means 20 being adjacent an upstream side of the spring-loaded valve seal 14 permits substantially only the heated valve seal 14, valve seating 72 and casing interior downstream thereof are contacted with released sample, so that loss of the trace sample is minimal and is encountered substantially only in a relatively small portion of the casing interior adjacent the outlet 2, so that (g) for purging the apparatus it is only necessary for purging gas to be passed into the purging gas inlet 6 with the valve seal 14 closed against the valve seating 72, so that only the relatively small portion of casing interior is purged.

The valve seating 72 is a chamfered portion of the interior of the casing 1 and enlarges in the downstream direction, and the valve seal 14 has a truncated-cone-shaped sealing surface 70 which seals against the chamfer.

The tubular casing 1 comprises an outer heat retaining, steel, tubular body 28, a stainless steel liner 30 in the bore of the body and in heat conductive contact with the body 28, and screw threaded collars 32 and 34 which are provided with O-ring seals 36 to 38. The steel outer body 28 has a pocket 40 for the cartridge heater 26 and another pocket 42 for a thermocouple 44.

The screw threaded collars 32 and 34 are screw threaded on to threaded portions 46 and 48 respectively of the steel outer body 28. The O-ring seal 36 seals the lower portion 2 of the stainless steel liner 30 to the steel outer body 28. The O-ring seal 37 seals an upper portion of the stainless steel liner 30 in the steel outer body 28. The O-ring seal 38 seals the screw threaded collar 34 to the steel outer body 28.

The screw threaded collar 34 has an extension 50 forming an extension of the sorbent tube receiving end portion 4 of the casing 1. The extension 50 is provided with a spring-loaded ball catch 52 which engages in a recess 54 in the sorbent tube 16 in the sample release position. The extension 50 is also provided with means for dissipating heat in the form of external heat exchange fins 55.

The spring loaded valve 14 comprises a valve stem 56 with grooves 62, 64, 66 and 68 therealong, the truncated-cone-shaped sealing surface 70 and a compression spring 58. The truncated-cone-shaped sealing surface 70 seals against chamfered internal seating 72 in the stainless steel liner 30. The compression spring 58 is compressed between a stepped portion 74 downstream of the truncated-cone-shaped valve sealing surface 70 and a step 76 in the bore 10 of the lower portion 2 of the stainless steel liner 30 to urge the cone-shaped valve seal 70 into sealing contact with the chamfered internal seating 72.

In operation, with the apparatus as shown in FIG. 1, it is placed to extend through the wall of an oven (not shown) of a gas chromatograph between the screw threaded collars 32 and 34. The tubular casing 1 is connected by the screw threaded, downstream end portion 2 to a sample analyzing apparatus (not shown), which in this instance is in the form of a gas chromatograph, and nitrogen is circulated as a purging gas through the inlet 6 and through the gas chromatograph with the solenoid valve 18 open. The cartridge heater 26 is used to heat the body 28, the valve 14 and the liner 30 to the desired temperature for releasing a sample from the sorbent tube 16.

Figure 3:
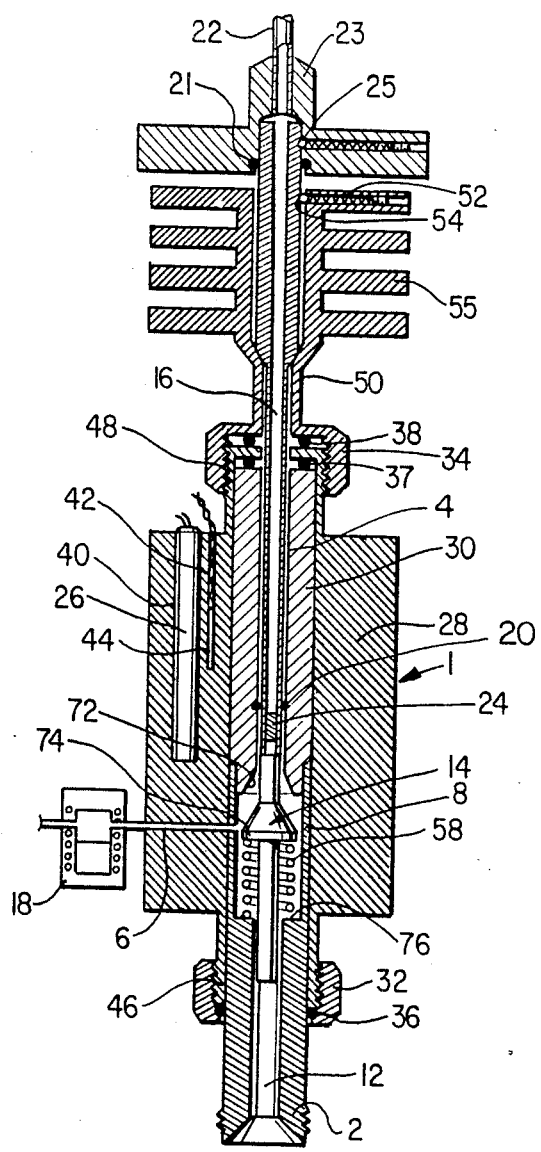
FIG. 3 is a similar view to FIG. 1 with a sorbent tube inserted in the apparatus to a sample release position therein.

The sorbent tube 16, with a heat releasable sample held on the carrying end 24 by the adsorption and/or absorption, is inserted in the sorbent tube receiving end portion 4 to open the spring loaded valve 14 and sit in the sample release position shown in FIG. 3. Nitrogen as a carrier gas is fed through tube 22 of the carrier gas connector 23 to which sorbent tube 16 is releasably attached, by means of the spring-loaded ball catch 25 and O-ring seal 21. The sorbent tube 16 is releasably secured in the sample release position by the spring loaded ball catch 52 and is sealed in the lining 30 by O-ring seal 20 at a position adjacent an upstream side of the valve seal 14.

The solenoid valve 18 is then closed and as the sample is released from the carrying end 24 by the heat from the body 28 and liner 30 it is conveyed into the gas chromatograph, for analysis, by entrainment in the carrier gas being introduced along the tube 22 into the tubular casing 1, and, after the entrainment, passing along the grooves 62, 64, 66 and 68.

Only the portion of the casing interior downstream of the O-ring seal 20 comes into contact with the entrained sample and so sample loss is negligible and is reduced by the casing interior being heated.

When the gas chromatograph has analyzed the sample, the sorbent tube 16 is removed from the sorbent tube receiving end portion 4 and the spring loaded valve 14, is closed against the valve seating 72, and the solenoid valve 18 is opened again to purge only the portion of the casing interior 8 downstream of the valve 14 together with the interior of the gas chromatograph. Any loss of sample between the O-ring seal 20 and the downstream end of the valve seating 72 is minuscule.

Figure 2:
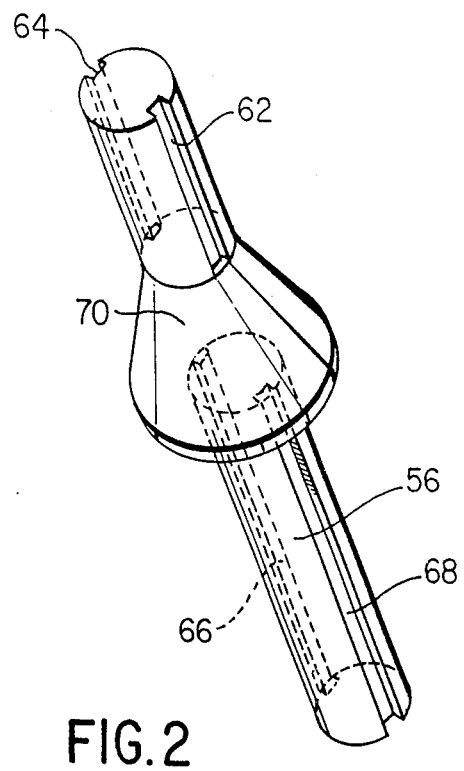
FIG. 2 is a perspective view of a valve stem of a spring loaded valve shown in FIG. 1.

The low loss of the sample and the excellent reproducibility of the chromatographic retention times using apparatus shown in FIGS. 1 to 3 was demonstrated in tests by depositing with a syringe sample in the form of known, small amounts of cocaine, heroin, 2,3,4,5,6-pentachlorobiphenyl, Aldrin (1,2,3,4,10,10-hexachloro-1,4,4a,5,8,8a-hexahydro-1,4:5,8-dimethanonapthalene), and ethylene glycol dinitrate in a suitable solvent such as acetone or hexane, on the sorbent tube receiving end portion and then analyzing the samples as described above. In each case, the recorded peak retention time was compared with that obtained with a conventional septum injection; the results are given in the following Tables I and II. These results indicate that apparatus according to the present invention can be used for introducing trace samples collected on the sorbent tube receiving end directly into a gas chromatograph for analysis thus eliminating the solvent elution step.

In some embodiments of the present invention a microswitch may be provided which is actuated automatically upon insertion/withdrawal of the sorbent tube 16 in or out of the receiving end portion 4 to control the solenoid valve 18.

It will be self-evident to anyone skilled in the art that thsi apparatus can advantageously be used with trace samples collected by commercially available sorbent sample tubes.

TABLE 1

COMPARISON OF RETENTION TIMES

| COMPOUND & quantity injected | Conventional Septum (using syringe) | | | Apparatus of FIGS. 1 to 3 | | |
|---|---|---|---|---|---|---|
| | Retention time (Min) | S.D. | Rel. S.D. (%) | Retention time (Min) | S.D. | Rel. S.D. (%) |
| Cocaine HCl 50 ng | 0.69 0.68 0.68 0.67 | | | 0.69 0.68 0.67 0.67 | | |
| | $\bar{x}$ = 0.68 | 0.0082 | 1.2 | $\bar{x}$ = 0.677 | 0.0096 | 1.42 |
| Heroin HCl 50 ng | 2.11 2.10 2.09 2.10 | | | 2.13 2.09 2.09 2.09 | | |
| | $\bar{x}$ = 2.10 | 0.008 | 0.38 | $\bar{x}$ = 2.10 | 0.02 | 0.95 |

Gas Chromatograph Conditions
Column: 45 × 0.32 cm (Nickel tube) 3% OV-1 on Chromosorb W
Detector(NPD): 250° C.
Injector Temp: 250° C.
Oven Temp: 205° C.
Carrier gas (N$_2$): 40 cc/min

TABLE 2

COMPARISON OF RETENTION TIMES

| COMPOUND QUANTITY INJECTED | CONVENTIONAL SEPTUM USING SYRINGE | | | APPARATUS OF FIGS. 1 TO 3 | | | GAS CHROMATOGRAPH CONDITIONS |
|---|---|---|---|---|---|---|---|
| | Retention time (min) | S.D. | Rel S.D. (%) | Retention time (min) | S.D. | Rel S.D. (%) | |
| 2,3,4,5,6-Pentachlorobiphenyl 1.0 ng | 1.02 1.03 1.05 1.04 | | | 1.06 1.02 1.05 1.05 | | | Column: Megabore DB-1, 10 m × 0.53 mm I.D. Detector (ECD): 250° C. Injector Temp.: 250° C. Oven Temp: 220° C. Carrier gas (N$_2$): 40 cc/min |
| | $\bar{x}$ = 1.03 | 0.008 | 0.79 | $\bar{x}$ = 1.04 | 0.017 | 1.65 | |
| Aldrin 400 pg | 0.63 0.62 0.63 | | | 0.62 0.63 0.63 | | | Column: Megabore DB-1, 10 m × 0.53 mm I.D. Detector (ECD): 250° C. Injector Temp.: 250° C. |

TABLE 2-continued

| | COMPARISON OF RETENTION TIMES | | | | | | |
|---|---|---|---|---|---|---|---|
| COMPOUND QUANTITY INJECTED | CONVENTIONAL SEPTUM USING SYRINGE | | | APPARATUS OF FIGS. 1 TO 3 | | | GAS CHROMATOGRAPH CONDITIONS |
| | Retention time (min) | S.D. | Rel S.D. (%) | Retention time (min) | S.D. | Rel S.D. (%) | |
| Ethylene Glycol Dinitrate (EGDN) 40 pg | 0.63 $\bar{x}$ = 0.627 1.48 1.48 1.49 1.48 $\bar{x}$ = 1.48 | 0.005 0.005 | 0.8 0.34 | 0.64 $\bar{x}$ = 0.63 1.48 1.49 1.48 1.48 $\bar{x}$ = 1.48 | 0.008 0.005 | 1.3 0.34 | Oven Temp: 220° C. Carrier gas (N$_2$): 40 cc/min Column: 60 cm × 0.32 cm (Nickel tube) ULTRABOND PEGS. Detector(ECD): 140° C. Injector: 140° C. Oven Temp: 125° C. Carrier gas(N$_2$): 40 cc/min |

We claim:

1. A sorbent tube trace sample releasing apparatus comprising:
   (A) tubular casing having:
     (1) a sample outlet end for connecting to a sample analyzing apparatus;
     (2) a sorbent tube receiving end for receiving and passing a sorbent tube;
     (3) a bore connecting said ends; and
     (4) a valve seat disposed in said bore;
   (B) a valve having:
     (1) an elongated valve stem extending in said bore and entirely disposed between said valve seat and said sample outlet end;
     (2) a valve seal fixedly attached to one end of the valve stem and engagable with said valve seat; and
     (3) spring means associated with said valve stem for urging said valve seal into engagement with said valve seat;
   (C) a purging gas inlet disposed through said tubular casing and being positioned between said valve seat and said sample outlet end and positioned such that when said valve seal is engaged with said valve seat, the purging gas inlet is between the valve seal and the sample outlet end, said purging gas inlet having associated therewith a valve for opening and closing said purging gas inlet;
   (D) a sorbent tube having sorbent therein and having a length and configuration so that a first trace sample receiving end is passable from said sorbent tube receiving end, through said bore and is engagable with said valve seal while an opposite end thereof protrudes from said sorbent tube receiving end;
   (E) a carrier gas connecting means for connecting the said sorbent tube opposite end with a carrier gas supply for passing a carrier gas through said sorbent tube;
   (F) sorbent tube sealing means for passing therethrough and sealing said sorbent tube in said bore when the said first end of the sorbent tube is engaged with said valve seal, said sealing means being disposed in said bore between said valve seat and said sorbent tube receiving end, but nearer said valve seat; and
   (G) a heating means associated with said casing for heating said casing, the valve seal and at least the first end of the sorbent tube when said first end is engaged with said valve seal;
   wherein the said first end of the sorbent tube is engagable with and can displace the valve seal from the valve seat by urging the valve stem against the spring means toward said sample outlet end, the heating means can heat and release a trace sample contained in the sorbent tube, and a carrier gas can pass through said sorbent tube and convey the released trace sample through said valve seat, said bore, out of said sample outlet end and into said sample analyzer;
   whereby substantially only the valve seat, valve seal and bore between the valve seat and sample outlet end contact said released trace sample, a purging gas passing through said purging gas inlet contacts substantially only the bore between the valve seal and sample outlet end, and, therefore, the loss of trace sample in the said trace sample releasing apparatus is minimized.

2. The apparatus of claim 1 wherein the valve seat is a chamfered portion of the bore of the casing and the valve seal has a truncated-cone-shaped sealing surface which is engagable with and seals against said chamfered portion.

* * * * *